Oct. 8, 1974 F. W ANDERSON Plant Pat. 3,633
NECTARINE TREE
Filed Aug. 15, 1973
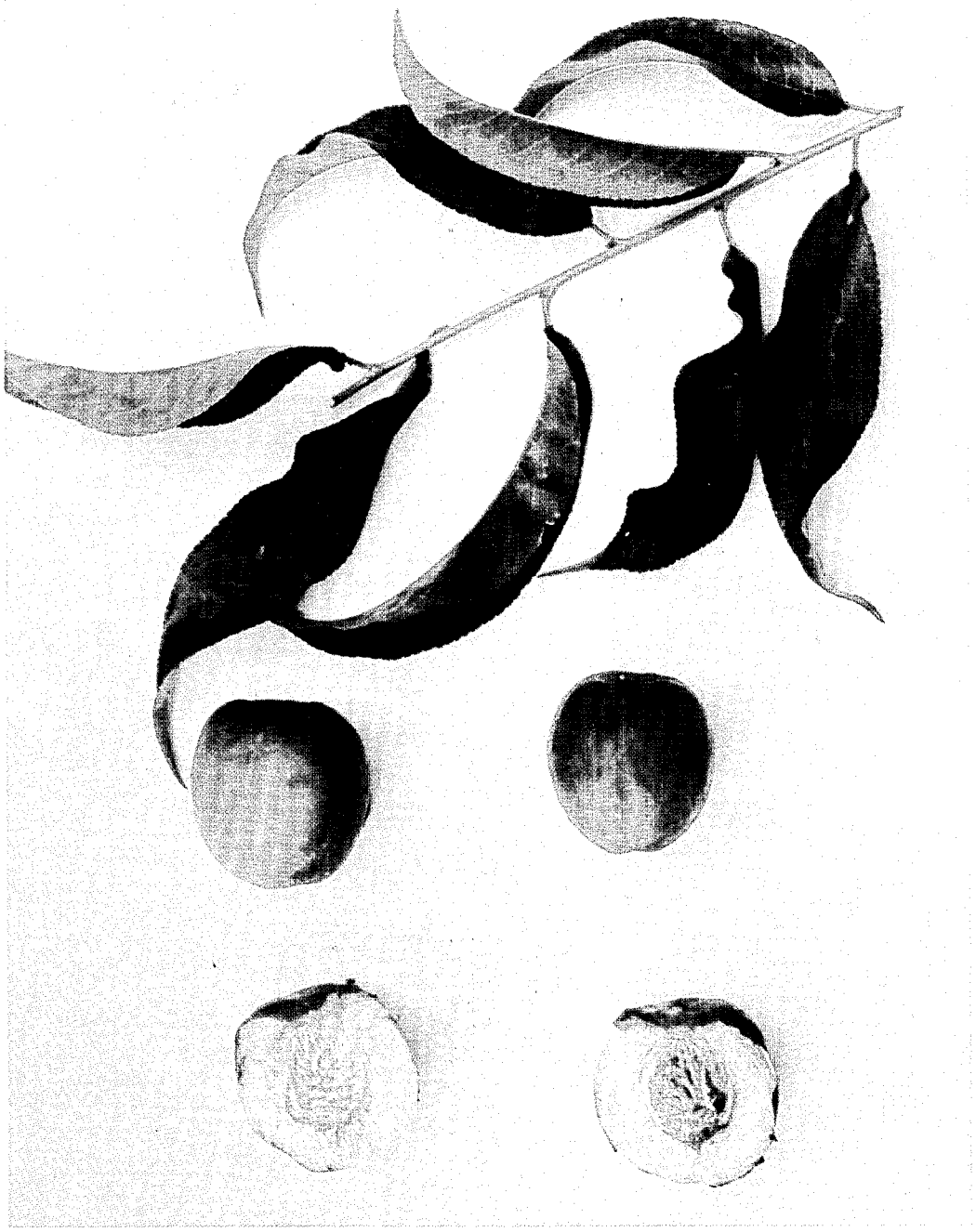

United States Patent Office

Plant Pat. 3,633
Patented Oct. 8, 1974

3,633

NECTARINE TREE

Frederic W. Anderson, Merced, Calif., assignor to Reedley Nursery, Inc., Reedley, Calif.

Filed Aug. 15, 1973, Ser. No. 388,565
Int. Cl. A01h 5/03
U.S. Cl. Plt.—41 1 Claim

ABSTRACT OF THE DISCLOSURE

A nectarine tree which is large, vigorous, upright, foliated with medium size, lanceolate leaves having a crenate margin, and a productive bearer of uniform, medium size, globose to oblong, freestone fruit having yellow skin substantially entirely overspread with a deep red, and yellow flesh.

Background of the variety: Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

Origin of the variety: The present variety of nectarine tree was originated by me, in my experimental nursery and orchard located as aforesaid, as an open-pollinated seedling of the Red June nectarine (U.S. Plant Pat. No. 2,044).

Asexual reproduction of the variety: Upon recognition by me of a novel and distinctive characteristic (as will hereinafter appear) of the present variety of nectarine tree, I asexually reproduced it by grafting on mature orchard trees in my said experimental orchard, and in maturity such reproductions ran true to the parent tree in all respects.

Summary of the variety: The present variety of nectarine tree is large, vigorous, upright, foliated with medium size, lanceolate leaves having a crenate margin, and a productive bearer of uniform, medium size, globose to oblong, freestone fruit having yellow skin substantially entirely overspread with a deep red, and yellow flesh; the variety—while generally resembling the Red June nectarine—being distinctively characterized by fruit ripening about one week earlier.

Brief description of the drawing: The drawing is an illustration, by photographic reproduction in color, of a twig with leaves, and separate fruit; one of the latter being cut in half to expose the flesh, and the stone remaining in one of the halves.

Description of the variety: The botanical details of this new and distinct variety of nectarine tree—with color definitions (except those in common color terms) referenced to Maerz and Paul Dictionary of Color—are as follows:

Tree
- *Size.*—Large.
- *Vigor.*—Vigorous.
- *Growth.*—Upright.
- *Production.*—Very productive.
- *Bearing.*—Regular bearer.

Trunk
- *Size.*—Medium.
- *Texture.*—Medium.

Branches
- *Size.*—Medium.
- *Texture.*—Medium.

Leaves
- *Size.*—Large to medium. Average length—6½". Average width—1½".
- *Form.*—Lanceolate.

- *Thickness.*—Medium
- *Texture.*—Smooth.
- *Margin.*—Crenate.
- *Petiole.*—Medium length.
- *Glands.*—Average number—4. Reniform. Usually positioned 2 on blade and 2 on petiole.
- *Color.*—Top side—Medium green (22–L–9). Under side—Lighter green (21–L–7).

Flower buds
- *Size.*—Medium.

Flowers
- *Blooming Period.*—About with Red June nectarine. Medium, as compared with other varieties.
- *Size.*—Large.
- *Color.*—Pink.

Fruit
- *Maturity When Described.*—Hard ripe—June 10th, 1973.
- *Date Of First Picking.*—June 1st, 1973.
- *Date Of Last Picking.*—June 10th, 1973.
- *Size.*—Uniform. Medium. Average diameter axially—2¼". Average transversely in suture plane—25/16".
- *Form.*—Globose to oblong.
- *Suture.*—Distinct. Extends from base to apex.
- *Ventral Surface.*—Rounded slightly.
- *Cavity.*—Elongated in suture plane. Average depth—½". Average breadth—⅝".
- *Apex.*—Very short. Depressed.

Skin
- *Thickness.*—Medium.
- *Tendency To Crack.*—None noted.
- *Down.*—Wanting.
- *Color.*—Yellow (11–L–5) substantially entirely overspread with deep red (7–L–6).

Flesh
- *Texture.*—Medium. Crisp. Melting.
- *Ripens.*—Evenly.
- *Flavor.*—Sub-acid.
- *Eating Quality.*—Fair to good.
- *Color.*—Yellow (10–K–2).

Stone
- *Type.*—Free.
- *Size.*—Medium. Average length—1⅝". Average breadth—⅞". Average thickness—¾".
- *Color.*—Beige (11–I–6).

Use
- Market—local Dessert.

Keeping quality: Medium.

Resistance to insects and diseases: No unusual susceptibilities noted.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, which is large, vigorous, upright, foliated with medium size, lanceolate leaves having a crenate margin, and a productive bearer of uniform, medium size, globose to oblong, freestone fruit having yellow skin substantially entirely overspread with a deep red, and yellow flesh; the variety—which resembles the Red June nectarine—being distinctively characterized, in comparison, by fruit which ripens about one week earlier.

No references cited.

ROBERT E. BAGWILL, Primary Examiner